United States Patent [19]

Bajgrowicz et al.

[11] Patent Number: 5,707,961
[45] Date of Patent: Jan. 13, 1998

[54] ODORANT COMPOUNDS AND COMPOSITIONS

[75] Inventors: Jerzy A. Bajgrowicz, Zurich; Alain Bringhen, Croix-de-Rozon; Georg Frater, Winterthur; Urs Müller, Zurich, all of Switzerland

[73] Assignee: Givaudan-Roure (International) SA, Vernier-Geneve, Switzerland

[21] Appl. No.: 638,008

[22] Filed: Apr. 25, 1996

[30] Foreign Application Priority Data

May 16, 1995 [CH] Switzerland ................. 1417/95

[51] Int. Cl.$^6$ ........................ A61K 7/46
[52] U.S. Cl. ............... 512/17; 512/24; 568/277; 568/343; 568/374
[58] Field of Search ............ 512/17, 24; 568/277, 568/343, 324

[56] References Cited

U.S. PATENT DOCUMENTS

| 2,933,506 | 4/1960 | Ohloff | 512/17 |
| 3,076,022 | 1/1963 | Kitchens | 512/17 |
| 3,929,677 | 12/1975 | Hall et al. | 512/17 |
| 5,180,709 | 1/1993 | Etzweiler et al. | 512/17 |

FOREIGN PATENT DOCUMENTS

| 464357 | 1/1992 | European Pat. Off. | 512/17 |

OTHER PUBLICATIONS

Mousseron–Canet et al, Chem. Abst., vol. 54, #2402, 1960.
M. Mousseron–Canet et al., Bull. Soc. Chim. France 601 seq. (1959).
Ulrich A. Huber, Soaps—Oils—Fats—Waxes 110, No. 15 (1984) 448–451 (with abstract).

*Primary Examiner*—James H. Reamer
*Attorney, Agent, or Firm*—George W. Johnston; Alan P. Kass; Mark E. Waddell

[57] ABSTRACT

The invention is concerned with novel odorants, including the compounds of the formula

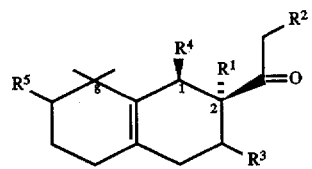

wherein
$R^1=R^4=CH_3$ and $R^2=R^3=H$ or
$R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=-CH_2-$ or
$R^1=CH_3$ and $R^2=R^3=H$ and $R^4=CH_2CH_3$ or
$R^1=R^2=R^4=CH_3$ and $R^3=H$ and $R^5=H$ (preferred) or $CH_3$.

5 Claims, No Drawings

ODORANT COMPOUNDS AND COMPOSITIONS

The invention is concerned with novel odorants, processes for their synthesis and odorant compositions employing them. More particularly, the invention concerns compounds of the formula:

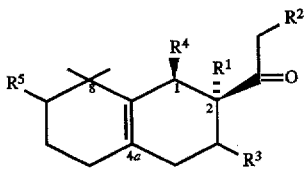
I wherein $R^1=R^4=CH_3$ and $R^2=R^3=H$ or
$R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=13$ $CH_2-$ or
$R^1=CH_3$ and $R^2=R^3=H$ and $R^4=CH_2CH_3$ or
$R^1=R^2=R^4=CH_3$ and $R^3=H$ and $R^5=H$ (preferred) or $CH_3$.

Formula I is also intended to embrace the possible enantiomers and the racemates when $R^3=R^5=H$ and the diastereomers in the case of substituents $R^3$ and $R^5$.

The invention is also concerned with odorant compositions containing I and with the use of I as odorants.

The compound of the formula

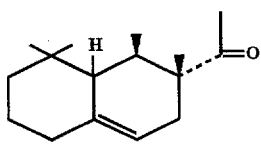
VI has, inter alia, become known as an odorant from EP 464 357, Example 5.

Displacement of the double bond D 4,4a to D 8,4a in this compound VI leads to the almost odorless compound, the diastereomer of the formula

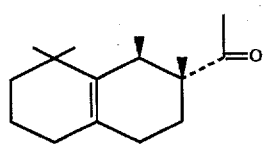
VII

Alteration of the stereochemistry at $C_1$ or $C_2$ surprisingly leads to a novel, extremely olfactory-intense compound of the formula

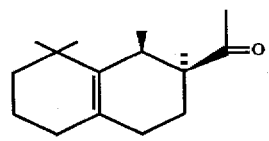
I' having interesting olfactory properties.

Such olfactory properties belong quite generally to the compounds of the formula

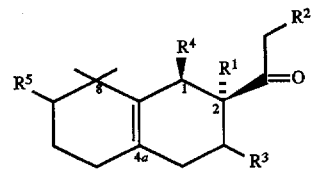
I

The compounds I are accessible by cyclizing the compounds

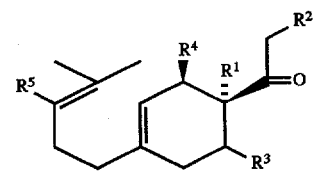
II under acidic conditions.

The convenient route to the compound II can be illustrated as follows on the basis of the compound of Example 1 hereinafter starting from geranial via homogeraniol, homomyrcene and then by its Diels-Alder reaction with a dienophilic carbonyl compound, especially with isopropenyl methyl ketone:

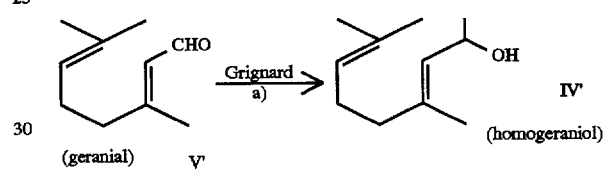

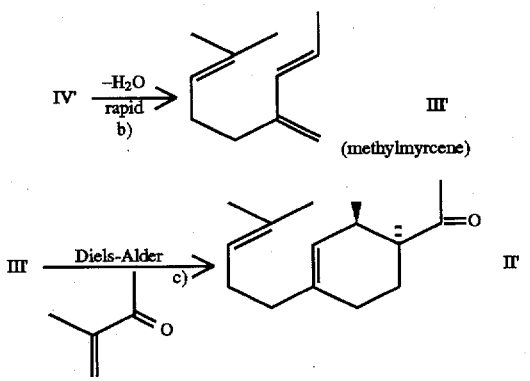

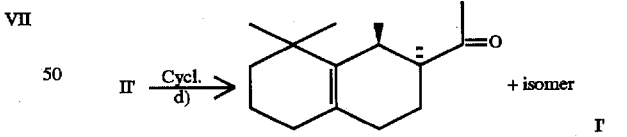

The suitable reaction conditions are:

a) The Grignard reaction using $CH_3MgX$ can be effected in a manner known to a person skilled in the art, i.e. $X=Cl$, Br, I and in usual inert solvents, e.g. tetrahydrofuran, etc., and at the usual temperatures.

b) The water cleavage is conveniently effected by iodine catalysis, with the iodine crystals being dissolved in IV' and this reagent being added dropwise in small portions at an elevated temperature, namely to a hydrocarbon, e.g. paraffin oil, heated to about 80° to about 120° C., and the III' formed being continuously distilled off.

c) The Diels-Alder reaction can be effected in a manner which will be well-known to a person skilled in the art, i.e. under the influence of the usual Lewis acids such as e.g. $AlCl_3$, $SnCl_2$, $TiCl_4$, $BF_3$, $BF_3$ complexes etc. Suitable solvents are aromatics or aliphatics such as benzene, toluene, cyclohexane, methylcyclohexane, chlorinated hydrocarbons such as chloroform, methylene chloride, etc. The temperature is conveniently about −20° C. to about +50° C.

d) The cyclization is conveniently effected under strong acidic conditions, with mineral acids or strong organic acids coming into consideration. $H_3PO_4$, especially crystallized phosphoric acid, stands in the foreground. Solvents are especially those mentioned above. The temperature conveniently lies in a range of about 100° C. to about 120° C.

Various like reaction procedures have become known from M. Mousseron-Canet et al., Bull. Soc. Chim. France 601 seq. (1959).

The structure of the end products is denoted there on page 603, column 2, as

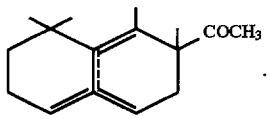

VIII

In a re-working it has, however, been found that there results almost exclusively the 1,2,4-trimethyl-1-acetyl-5-isopentenylcyclohex-3-ene of the formula

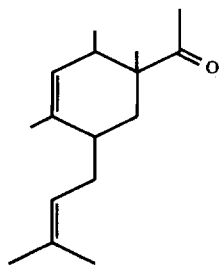

IX to which the very vague names "gem-dimethyl-1-methyl-8-methyl-1-ethylone octaline-9", page 606, column 1 (step d) or isohexyl-4-methyl-2-methyl-1-ethylone-cyclohexene-4 (step c) can not by any means be applied.

The reasoning is that a) in the known case starting from citral, a mixture of geranial and neral is accordingly used,

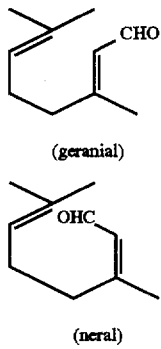

(geranial)

(neral)

and b) in the water cleavage from, inter alia, the homogeraniol (IV', page 600, column 1) there does not result the desired homomyrcene, III', page 600, column 2, but mainly the isomeric homoocimene

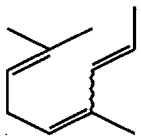

X which product X leads in (steps c) and d) to the mono-cyclic compound

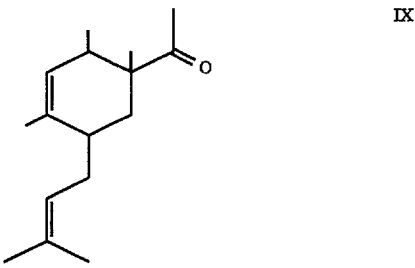

IX which is of absolutely no interest from the olfactory point of view.

These conclusions follow from the results of a precise re-working of the corresponding steps of Mousseron et al identified above.

Finally, with respect to the fragrant derivatives generically referred to by Mousseron et al. on page 603, column 2, line 30, having regard to the results of the re-working it has to be assumed that here just homoocimene derivatives, i.e. monocyclic derivatives of compound X, must have been involved.

As stated above, the invention is also concerned with the use of compounds I as odorants.

The compounds I are distinguished by a powerful, diffusive and very natural-warm notes in the direction of wood and amber.

Having regard to their natural olfactory notes, the compounds of formula I are especially suitable for modifying known compositions. Their extraordinary olfactory strength should, in particular, be emphasized: the olfactory threshold value of I' is ~0.1 ng/l; the olfactory value is 150,000. With respect to the definition of olfactory value and olfactory threshold value see e.g. Ulrich A. Huber, Soaps—Oils—Fats—Waxes 110, No. 15 (1984) 448–451.

The compounds I combine with numerous known odorant ingredients of natural or synthetic origin, whereby the range of the natural raw materials can embrace not only readily-volatile but also moderately-volatile and difficultly-volatile components and that of the synthetics can embrace representatives from practically all classes of substance, as will be evident from the following compilation:

Natural products, such as tree moss absolute, basil oil, agrumen oils (such as bergamot oil, mandarine oil, etc.), mastix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, aldehdydes, such as citral, Helional®, α-hexylcinnamaldehyde, hydroxycitronellal, Lilial® (p-tert.butyl-α-methyldihydrocinnamaldehyde), methylnonylacetaldehyde, ketones, such as allylionone, α-ionone, β-ionone, isoraldein (isomethyl-α-ionone), methylionone, esters, such as allyl phenoxyacetate, benzyl salicylate, cinnamyl propionate, citronellyl acetate, citronellyl ethoxalate (citronellyl . O—CO—CO . $OC_2H_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate.

lactones, such as γ-undecalactone, various components frequently used in perfumery, such as musk ketone, indole, p-menthane-8-thiol-3-one, methyleugenol.

Further, the manner in which the compounds I round-off, harmonize and enrich the olfactory notes of known compositions without dominating in an unpleasant manner is remarkable. The strength, adhesion (tenacity), warmth, substantivity and volume of these compounds should also be emphasized in particular.

The compounds of formula I (and, respectively, mixtures thereof) can be used in wide limits which in compositions can extend, for example, from 0.1 (detergents)–5% (alcoholic solutions), without these values being limiting values, since the experienced perfumer can also produce effects with even lower concentrations or can synthesise novel complexes with even higher amounts. The preferred concentrations range between about 0.2 and 2%. The compositions produced with I can be used for all kinds of perfumed consumer goods (eau de Cologne, toilet water, extracts, lotions, creams, shampoos, soaps, salves, powders, toothpastes, mouth washes, deodorants, detergents, tobacco, etc.).

The compounds can accordingly be used in the production of compositions and—as will be evident from the above compilation—a wide range of known odorants or odorant mixtures can be used. In the production of such compositions the known odorants enumerated above can be used according to methods known to the perfumer, such as e.g. from W. A. Poucher, Perfumes, Cosmetics and Soaps 2, 7th edition, Chapman and Hall, London, 1974.

The compounds of formula II also possess the olfactory properties enumerated above; they can accordingly be used analogously.

EXAMPLE 1 a) 4,8-Dimethyl-2-hydroxy-nona-3,7-diene (IV')

1 l of t-butyl methyl ether and 1.05 l of 3N methyl magnesium chloride solution were placed under $N_2$ in a 4½ l sulphonation flask having a thermometer, stirrer and dropping funnel and 456 g of geranial in 500 ml of t-butyl methyl ether were added dropwise at 0° C. The mixture was stirred at 10° C. for 1 hour and poured on to 3 kg of ice and 500 g of $NH_4Cl$ and treated with 1 l of hexane. After mixing well the $H_2O$ phase was separated and washed neutral 3 times with 500 ml of $NH_4Cl$ solution, dried and evaporated.

Finally, drying was carried out at 0.5 mm Hg and 40° C., with 513 g of oil being obtained; crude yield 100% of theory.

b) 8-Methyl-4-methylidene-nona-2,7-diene (III')

120 g of paraffin oil were placed in a 1 l 2-necked flask having an internal thermometer. The flask was fitted with a Claisen headpiece, a dropping funnel with a long internal tube and a Vigreux column (60 cm long) having a good intensive condenser and stirring was carried out at 140°–147° C. internal temperature and 10–16 mm Hg. Then, a solution of iodine in alcohol IV' was added dropwise such that the temperature at the head of the column was 75°–80° C. The rate at which the dropwise addition was carried out was adjusted to 350–400 ml/h and the internal temperature was held at 145° C. The duration was 5½ hours, with always 200 g portions of the alcohol being mixed with 0.4 g of iodine under $N_2$. The hydrocarbon/$H_2O$ mixture was investigated periodically by gas chromatography (content of b) between 59% and 70%). The distillate was separated portionwise, the $H_2O$ phase was separated (pH 1–2), shaken with 15% NaOH and stored in a refrigerator on $K_2CO_3$. A total of 1780 g of yellow oil was obtained, content of b) 61.8%.

These 1780 g were distilled over a 70 cm Sulzer column in a high vacuum with the addition of 20 g of $K_2CO_3$ and thus the methylmyrcene was separated from the residue (the other hydrocarbons).

Total yield: 901 g of methylmyrcene (III') (90%) of b.p. 40°–42° C./0.12 mmHg (45% of the theoretical yield over two steps). The product was stabilized with 0.5% hydroquinone.

c) 1-Acetyl-1,2-dimethyl-4-(4-methyl-pent-3-enyl)cyclohex-3-ene (II')

40 g of $AlCl_3$ were placed in 1.3 l of methylene chloride under $N_2$ in a 2½ l sulphonation flask. A mixture of 280 g of methylmyrcene (III') and 134.4 g of isopropenyl methyl ketone in 300 ml of methylene chloride was added dropwise while cooling well at ≦15° C. (duration 1 hr. 20 min.). [Alternatively, the diene can be added drop by drop into a solution of $AlCl_3$ and isopropenylmethylketone]. The mixture was stirred for 30 minutes and hydrolyzed on 1½ l of ice-water mixture. The mixture was washed neutral twice with $H_2O$, the last traces of acid were removed with $K_2CO_3$ solution (5%) and, after drying, it was evaporated. 430 g of yellow oil were obtained.

These 430 g were distilled over a 15 cm Vigreux column in a high vacuum, there being obtained 319 g of colorless oil of b.p. 98°–114° C. (85% of theory).

d) (1R*,2S*)-2-Acetyl-1,2,3,4,5,6,7,8-octahyrdo-1,2,8,8-tetramethylnaphthalene I' [and (2S*,3R*)-2-acetyl-1,2,3,4,5, 6,7,8-octahydro-2,3,8,8-tetramethylnaphthalene]

180 g of phosphoric acid were placed while gassing with $N_2$ in a 1½ l sulphonation flask having a thermometer, reflux condenser and stirrer and a solution of 310 g of ketone II' in 500 ml of toluene was added. The mixture was cooled to reflux (115° C.) while stirring and was stirred at this temperature for 30 min. Then, it was cooled rapidly and poured into 600 ml of ice/$H_2O$ and diluted with 1 l of hexane and extracted twice with $H_2O$, washed with 10% NaOH, dried and evaporated. There were obtained 325 g of oil.

When distilled in a high vacuum there were obtained 224.6 g of oil of b.p. 92°–96° C./0.09 mm Hg.

Yield of olfactorily good product 224.6 g (74.2% of theory).

Odor: amber-like, woody, tobacco.

EXAMPLE 2

In an analogous manner, from homomyrcene (III') and 2-methyl-2-cyclopenten-1-one via (3aRS,7SR,7aRS)-5-(4-methyl-pent-3-enyl)-7,7a-dimethyl-2,3,3a,4,7,7a-hexahydro-1H-inden-1-one there was obtained (3aRS,9SR,9aRS)-8,8,9,9a-tetramethyl-2,3,3a,4,5,6,7,8,9,9a-decahydro-1H-benz<f>inden-1-one.

Odor: amber-like, woody.

EXAMPLE 3

Also analogously, from homomyrcene (III') and 2-methylidene-1-cyclopentanone there was obtained via the spirocyclopentanone II the rac-1',2',3',4',5',6',7',8'-octahydro-1'alpha,8',8'-trimethyl-spiro[cyclopentane-(alpha2), 2'(1'H)-naphthalene-]-2-one.

Odor: woody, amber-like, after sclareol.

EXAMPLE 4

Finally, 2-acetyl-1,2,3,4,5,6,7,8-octahydro-1,8,8-trimethylnaphthalene was accessible from homomyrcene (III') and methyl vinyl ketone via 1-acetyl-2-methyl-4-(4-methyl-pent-3-enyl)-cyclohex-3-ene.

Odor: dry, woody, amber-like.

EXAMPLE 5 rac-2α-Acetyl-1α-ethyl-1,2,3,4,5,6,7,8-octahydro-2,8,8-trimethylnaphthalene was obtained from ethylmyrcene (bishomomyrcene) analogously to Example 1.

Odor: woody, amber-like.

EXAMPLE 6 rac-2α-Propionyl-1,2,3,4,5,6,7,8-octahydro-1α,2,8,8-tetramethylnaphthalene was also obtained analogously to Example 1, but by reacting methylmyrcene with isopropenyl ethyl ketone.

Odor: woody, amber-like.

EXAMPLE 7

|  | Parts by weight |
|---|---|
| a) Toilet water for women | |
| Cyclohexal | 54.0000 |
| Dipropylene glycol | 348.2000 |
| Galaxolide 50 BB (1,3,4,6,7,8-hexahydro-4,6,6,7,8,8-hexamethyl-cyclopenta-γ-2-benzopyran) | 262.0000 |
| Compound I' | 37.0000 |
| Hedione (methyl dihydrojasmonate) | 55.0000 |
| Heliotropin cryst. | 11.0000 |
| Isoraldein 95 (isomethyl-a-ionone) | 206.0000 |
| Linalool synt. | 1.0000 |
| Pêche pure (γ-undecalactone) | 1.8000 |
| Radjanol (bagdanol) (1-β-hydroxymethyl-2-pentenyl)-2,2,3-trimethyl-cyclopent-3-ene) | 8.0000 |
| Vanillin | 16.0000 |
|  | 1000.0000 |
| b) Toilet water for men | |
| Phenyl-ethyl alcohol | 2.0000 |
| Allyl amyl glycolate | 18.0000 |
| Ambroxan (3-methyldodecahydro-6,6,9A-trimethyl-naphth-2,1B-furan) | 3.0000 |
| Bergamot essence | 130.0000 |
| Carbitol (diethylene glycol monoethyl ether) | 20.0000 |
| Lemon essence | 20.0000 |
| Citronellol | 3.0000 |
| Cyclohexal | 10.0000 |
| α-Damascone | 4.0000 |
| Dihydro-myrcenol | 150.0000 |
| Evernyl (methyl β-orcinecarboxylate) | 5.0000 |
| Fixolide (1,1,2,4,4,7-hexamethyl-6-acetyl-1,2,3,4-tetrahydro-naphthalene) | 70.0000 |
| Galbex 183 (composition in the direction of galbanum) | 3.0000 |
| Geranium essence | 5.0000 |
| Compound I' | 7.0000 |
| Hedione | 55.0000 |
| Fixateur Hercolyn (dihydroltetrahydro-methylabietate) | 25.0000 |

-continued

|  | Parts by weight |
|---|---|
| Hydroxycitronellal | 20.0000 |
| Isoraldein 40 | 5.0000 |
| Lavandin | 50.0000 |
| Lemarome N (neral-citral mixture) | 3.0000 |
| Mandarine essence | 10.0000 |
| Methyl cedryl ketone | 80.0000 |
| Oranger cryst. (γ-undecalactone) | 2.0000 |
| Diethyl phthalate | 267.0000 |
| Precyclemone B (dehydrovemaldehyde) | 10.0000 |
| Rosmary essence | 10.0000 |
| Rosoflor 2 (geraniol-nerol mixture) | 3.0000 |
| Amyl salicylate | 5.0000 |
| Sandalore (3-methyl-5-(2,2,3-trimethyl-cyclopent-3-en-1-yl)-pentan-2-ol) | 5.0000 |
|  | 1000.0000 |
| c) Flowery-woody, slightly spicy aspect | |
| Benzyl acetate extra | 40.0000 |
| Dimethyl-benzyl-carbinyl acetate | 40.0000 |
| Geranyl acetate synt. | 30.0000 |
| Phenyl-ethyl alcohol | 100.0000 |
| Bergamot oil | 100.0000 |
| Cetone-α(α-methylionone) | 80.0000 |
| Cyclohexal | 40.0000 |
| Dipropylene glycol | 80.0000 |
| Eugenol | 20.0000 |
| Galaxolide 50 DEP | 40.0000 |
| Gardenol (phenyl-methyl-carbinyl acetate) | 10.0000 |
| Geraniol | 50.0000 |
| Compound I' | 20.0000 |
| Hedione | 40.0000 |
| Heliotropin cryst. | 20.0000 |
| Hydroxycitronellal | 50.0000 |
| Methyl cedryl ketone | 60.0000 |
| Methyl-isoeugenol | 10.0000 |
| Musk ketone | 50.0000 |
| Benzyl salicylate | 100.0000 |
| Thibetolide (Ω-pentadecalactone) | 20.0000 |
|  | 1000.0000 |

We claim:

1. Compounds of the formula

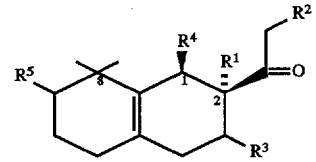

wherein $R^1 = R^4 = CH_3$ and $R^2 = R^3 = H$ or
$R^1 = R^2 = R^3 = H$ and $R^4 = CH_3$, or
$R^1 + R^2 = -CH_2CH_2-$ and $R^3 = H$ and $R^4 = CH_3$, or
$R^1 = R^4 = CH_3$ and $R^2 + R^3 = -CH_2-$ or
$R^1 = CH_3$ and $R^2 = R^3 = H$ and $R^4 = CH_2CH_3$ or
$R^1 = R^2 = R^4 = CH_3$ and $R^3 = H$ and $R^5 = H$ or $CH_3$.

2. Compounds of the formula

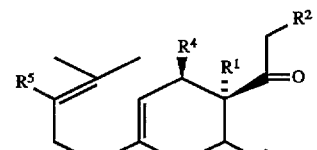

wherein $R^1 = R^4 = CH_3$ and $R^2 = R^3 = H$ or $R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=-CH_2-$ or
$R^1=CH_3$ and $R^2=R^3=H$ and $R^4=CH_2CH_3$ or
$R^1=R^2=R^4=CH_3$ and $R^3=H$ and $R^5=H$ or $CH_3$.

3. A process for the manufacture of the compounds

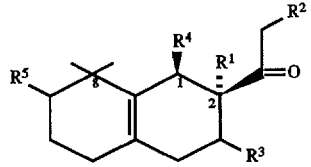    I wherein
$R^1=R^4=CH_3$ and $R^2=R^3=H$ or
$R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=-CH_2-$ or
$R^1=CH_3$ and $R^2=R^3=H$ and $R^4=CH_2CH_3$ or
$R^1=R^2=R^4=CH_3$ and $R^3=H$ and $R^5=H$ or $CH_3$,
which process comprises cyclizing a compound of the formula

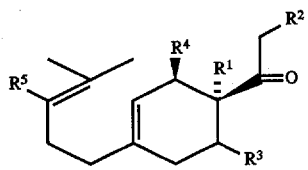    II under acidic conditions.

4. An odorant composition which contains a compound of the formula

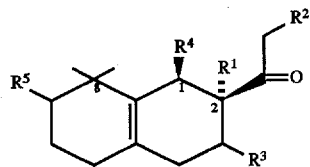    I wherein
$R^1=R^4=CH_3$ and $R^2=R^3=H$ or
$R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=-CH_2-$ or
$R^1=CH_3$ and $R^2=R^3=H$ and $R^4=CH_2CH_3$ or
$R^1=R^2=R^4=CH_3$ and $R^3=H$ and $R^5=H$ or $CH_3$.

5. An odorant composition which contains a compound of the formula

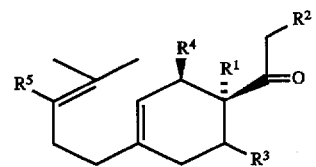    II wherein
$R^1=R^4=CH_3$ and $R^2=R^3=H$ or
$R^1=R^2=R^3=H$ and $R^4=CH_3$, or
$R^1+R^2=-CH_2CH_2-$ and $R^3=H$ and $R^4=CH_3$, or
$R^1=R^4=CH_3$ and $R^2+R^3=-CH_2-$ or
$R^1=CH_3$ and $R^2=R^3=H$ and $R^4=CH_2CH_3$ or
$R^1=R^2=R^4=CH_3$ and $R^3=H$ and $R^5=H$ or $CH_3$.

* * * * *